US00PP21250P2

(12) United States Plant Patent
Valenzuela et al.

(10) Patent No.: US PP21,250 P2
(45) Date of Patent: Aug. 31, 2010

(54) ***ALSTROEMERIA* PLANT NAMED 'JAVERONICA'**

(50) Latin Name: *Alstroemeria hybrida*
Varietal Denomination: Javeronica

(75) Inventors: Camilo Herrera Valenzuela, Bogotá (CO); Henry Belalcázar Valencia, Bogotá (CO)

(73) Assignee: C.I. Velmer S.A., Bogatá (CO)

( * ) Notice: Subject to any disclaimer, the term of this patent is extended or adjusted under 35 U.S.C. 154(b) by 0 days.

(21) Appl. No.: 12/383,843

(22) Filed: Mar. 27, 2009

(51) Int. Cl.
*A01H 5/00* (2006.01)

(52) U.S. Cl. ..... Plt./309

(58) Field of Classification Search ..... Plt./309
See application file for complete search history.

*Primary Examiner*—June Hwu
(74) *Attorney, Agent, or Firm*—C. A. Whealy

(57) ABSTRACT

A new and distinct cultivar of *Alstroemeria* plant named 'Javeronica', characterized by its erect and strong flowering stems; vigorous growth habit; red-colored flowers arranged in rounded symmetrical umbels; and excellent postproduction longevity.

1 Drawing Sheet

Botanical designation: *Alstroemeria hybrida.*
Cultivar Denomination: 'JAVERONICA'.

BACKGROUND OF THE INVENTION

The present invention relates to a new and distinct cultivar of *Alstroemeria* plant, botanically known as *Alstroemeria hybrida,* commercially used as a cut flower *Alstroemeria,* and hereinafter referred to by the name 'Javeronica'.

The new *Alstroemeria* plant is a product of a planned breeding program in Madrid, Cundinamarca, Colombia. The objective of the breeding program was to create new *Alstroemeria* cultivars with attractive flower color and good postproduction longevity.

The new *Alstroemeria* plant originated from a cross-pollination conducted by the Inventors in Madrid, Cundinamarca, Colombia in March, 2003 of a proprietary selection of *Alstroemeria hybrida* identified as code number JA 510, not patented, as the female, or seed, parent with a proprietary selection of *Alstroemeria hybrida* identified as code number JAH231, not patented, as the male, or seed, parent. The new *Alstroemeria* plant was discovered and selected by the Inventor as a single flowering plant from within the progeny of the stated cross-pollination grown in a controlled greenhouse environment in Madrid, Cundinamarca, Colombia in May, 2004.

Asexual reproduction of the new *Alstroemeria* plant by rhizome divisions in a controlled greenhouse environment in Madrid, Cundinamarca, Colombia since June, 2004, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Javeronica'.

These characteristics in combination distinguish 'Javeronica' as a new and distinct cultivar of *Alstroemeria* plant:

1. Erect and strong flowering stems.
2. Vigorous growth habit.
3. Red-colored flowers arranged in rounded symmetrical umbels.
4. Excellent postproduction longevity.

Plants of the new *Alstroemeria* can be compared to plants of the parent selections. Plants of the new *Alstroemeria* differ from plants of the parent selections primarily in flower color as plants of the parent selections have red purple and white bi-colored flowers.

Plants of the new *Alstroemeria* can be compared to plants of *Alstroemeria hybrida* 'Zalsatine', disclosed in U.S. Plant Pat. No. 15,251. In side-by-side comparisons conducted in Madrid, Cundinamarca, Colombia, plants of the new *Alstroemeria* differed primarily from plants of 'Zalsatine' in flower color. In addition, plants of the new *Alstroemeria* had larger flowers and shorter pedicels than plants of 'Zalsatine'.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria.*

The photograph in the center of the sheet comprises a side perspective view of a typical flowering stem of 'Javeronica'.

The photograph on the left side of the sheet is a close-up view of a typical flower umbel of 'Javeronica'.

The photograph on the top right of the sheet is a close-up view of a typical flower of 'Javeronica'.

The photograph on the bottom right of the sheet is a close-up view of the upper and lower surfaces of typical leaves of 'Javeronica'.

DETAILED BOTANICAL DESCRIPTION

The aforementioned photographs and following observations and measurements describe plants of the new *Alstroemeria* grown in Madrid, Cundinamarca, Colombia in a polyethylene-covered greenhouse in ground beds. During the production of the plants, day temperatures ranged from 10.5° C. to 31.5° C., night temperatures ranged from 6° C. to 8.5° C. and light levels averaged 21.4 KWH/$m^2$. Plants used for the photographs and description were 44 weeks old. Color references are made to The Royal Horticultural Society Colour Chart, 2001 Edition, except where general terms of ordinary dictionary significance are used.

Botanical classification: *Alstroemeria hybrida* 'Javeronica'.

Parentage:

*Female, or seed, parent.*—Proprietary selection of *Alstroemeria hybrida* identified as code number JA 510, not patented.

*Male, or pollen, parent.*—Proprietary selection of *Alstroemeria hybrida* identified as code number JAH231, not patented.

Propagation:

*Type.*—By rhizome divisions.

*Time to initiate roots.*—About two weeks at temperatures ranging from 8° C. to 29° C.

*Time to produce a rooted young plant.*—About eight weeks at temperatures ranging from 8° C. to 29° C.

*Root description.*—Fleshy, medium in thickness; close to 155A in color.

*Rooting habit.*—Freely branching; dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Upright; freely branching, bushy appearance; vigorous growth habit.

*Time from planting to harvest of cut flowers.*—About 126 days.

*Plant height.*—About 110 cm to 120 cm.

*Plant diameter* (*spread*).—About 15 cm.

Flowering stem description:

*Aspect.*—Erect.

*Length.*—About 110 cm to 120 cm.

*Diameter.*—About 7 mm.

*Internode length.*—About 4.4 cm.

*Strength.*—Strong.

*Texture.*—Smooth, glabrous.

*Color.*—Close to 144A.

Foliage description:

*Arrangement.*—Alternate, simple.

*Length.*—About 13.5 cm.

*Width.*—About 3.3 cm.

*Shape.*—Oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing and fully developed leaves, upper surface: Close to 137A to 137B; venation, close to 138A. Developing and fully developed leaves, lower surface: Close to 137C; venation, close to 138B.

*Petioles.*—Length: About 4.5 cm. Diameter: About 8 mm. Texture, upper and lower surfaces: Smooth, glabrous. Color, upper and lower surfaces: Close to 144A to 144B.

Flower description:

*Flower type and arrangement.*—Single cup-shaped flowers arranged in compound umbels; flowers face upright to outwardly; perianth segments separate.

*Flowering habit.*—Freely flowering with about 15 open flowers and flower buds per inflorescence.

*Natural flowering season.*—Flowering continuous year round in a greenhouse in Colombia; plants begin flowering about 126 days after planting.

*Fragrance.*—Not detected.

*Flower longevity as a cut flower.*—About 10 to 14 days; flowers not persistent.

*Flower buds* (*showing color*).—Length: About 5 cm. Diameter: About 1.6 cm. Shape: Oblanceolate to obovate. Color: Close to 185B.

*Umbel height.*—About 12 cm.

*Umbel diameter.*—About 15 cm by 18 cm.

*Flower diameter.*—About 6 cm.

*Flower length* (*height*).—About 5.7 cm.

*Flower depth.*—About 6.7 cm.

*Perianth.*—Arrangement: Six arranged in two whorls, each whorl with two lateral and one median segments. Outer perianth, lateral segments: Length: About 5.2 cm. Width: About 2.6 cm. Shape: Obovate. Apex: Embedded pointed. Base: Truncate. Margin: Entire; somewhat sinuate and erose. Texture, upper and lower surfaces: Smooth, glabrous. Color, when opening, upper surface: Close to 53A. Color, when opening, lower surface: Close to 187C; towards the apex and venation, close to 187A. Color, fully opened, upper surface: Close to 53A; color becoming closer to 60A to 60B with development. Color, fully opened, lower surface: Close to 53A; venation, close to 187A to 187B. Outer perianth, median segment: Length: About 5.5 cm. Width: About 2.8 cm. Shape: Obovate. Apex: Embedded pointed. Base: Truncate. Margin: Entire; somewhat sinuate and erose. Texture, upper and lower surfaces: Smooth, glabrous. Color, when opening, upper surface: Close to 53A. Color, when opening, lower surface: Close to 187C; venation, close to 187A. Color, fully opened, upper surface: Close to 53A; color becoming closer to 60A to 60B with development. Color, fully opened, lower surface: Close to 53A; venation, close to 187A to 187B. Inner perianth, lateral segments: Length: About 6.4 cm. Width: About 1.9 cm. Shape: Oblanceolate. Apex: Acuminate. Base: Truncate. Margin: Entire; slightly sinuate. Texture, upper and lower surfaces: Smooth, glabrous. Color, when opening, upper surface: Close to 185B. Color, when opening, lower surface: Close to 185A to 185B. Color, fully opened, upper surface: Towards the apex, close to 60C; towards the base, close to 186D; random streaks/flecks, close to 187A; color becoming closer to 60D with development. Color, fully open, lower surface: Towards the apex, close to 60B; towards the base, close to 186C to 186D. Inner perianth, median segment: Length: About 4.6 cm. Width: About 1.8 cm. Shape: Oblanceolate. Apex: Acuminate. Base: Truncate. Margin: Entire; slightly sinuate. Texture, upper and lower surfaces: Smooth, glabrous. Color, when opening, upper surface: Close to 185B to 185C. Color, when opening, lower surface: Close to 185B. Color, fully opened, upper surface: Towards the apex, close to 53C; towards the base, close to 54C to 54D; random streaks/flecks, close to 187A; color becoming closer to 60D with development. Color, fully open, lower surface: Towards the apex, close to 60B; towards the base, close to 60D.

*Peduncles.*—Length: About 17 cm. Diameter: About 6 mm. Strength: Strong. Angle: Erect. Texture: Smooth, glabrous. Color: Close to 144A.

*Pedicels.*—Length: About 7.3 cm to 7.6 cm. Diameter: About 3 mm. Strength: Strong. Angle: About 15° to 30° from the peduncle axis. Texture: Smooth, glabrous. Color: Close to 144A.

*Reproductive organs.*—Stamens: Quantity per flower: Six. Anther shape: Elliptical. Anther length: About 8 mm. Anther diameter: About 3 mm. Anther color: Close to 183A. Pollen amount: Moderate. Pollen color: Close to N200B. Pistils: Quantity per flower: One. Pistil length: About 6 cm. Style length: About 4.6 cm. Style color: Close to 60D. Stigma shape: Three-parted. Stigma color: Close to 60C. Ovary color: Close to 146B tinted with close to 187B.

*Fruit/seed.*—Fruit and seed development has not been observed.

Disease/pest resistance: Plants of the new *Alstroemeria* have not been observed to be resistant to pathogens and pests common to *Alstroemeria*.

Temperature tolerance: Plants of the new *Alstroemeria* have been observed to tolerate temperatures from about 6° C. to about 32° C.

It is claimed:

1. A new and distinct *Alstroemeria* plant named 'Javeronica' as illustrated and described.

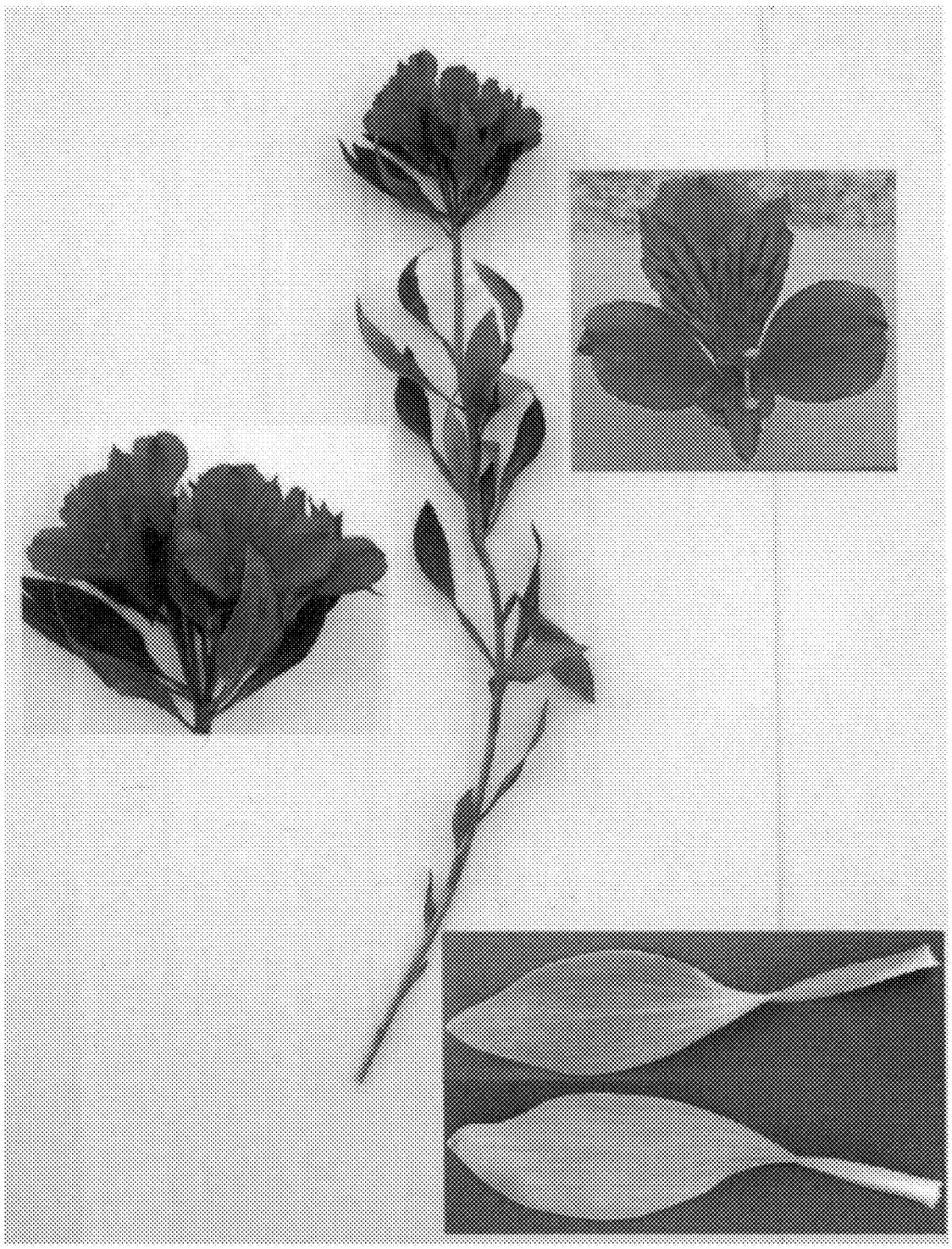

* * * * *